United States Patent [19]

Voloudakis

[11] Patent Number: 5,121,643
[45] Date of Patent: Jun. 16, 1992

[54] SOIL SAMPLING TOOL

[76] Inventor: John S. Voloudakis, 6837 E. Berneil, Scottsdale, Ariz. 85253

[21] Appl. No.: 620,560

[22] Filed: Dec. 3, 1990

[51] Int. Cl.⁵ .............................................. G01N 1/04
[52] U.S. Cl. ................................................. 73/864.41
[58] Field of Search ........... 73/864.41, 864.43–864.45, 73/864.51–864.61; 175/20, 58

[56] References Cited

U.S. PATENT DOCUMENTS

| | | | |
|---|---|---|---|
| 230,121 | 7/1880 | Frost | 73/864.64 |
| 3,080,760 | 3/1963 | Piersma . | |
| 3,091,968 | 6/1963 | Platzer . | |
| 3,109,307 | 11/1963 | Papworth . | |
| 4,252,200 | 2/1981 | Peterson | 175/20 |
| 4,442,721 | 4/1984 | Singer | 73/863 |
| 4,790,198 | 12/1988 | Awtry et al. | 73/864.64 |

Primary Examiner—Robert Raevis
Attorney, Agent, or Firm—Jordan M. Meschkow; Don J. Flickinger

[57] ABSTRACT

A cylindrical rod having an insertable end and a handle end, defining a plurality of collecting pockets located serially along its length.

2 Claims, 1 Drawing Sheet

U.S. Patent June 16, 1992 5,121,643
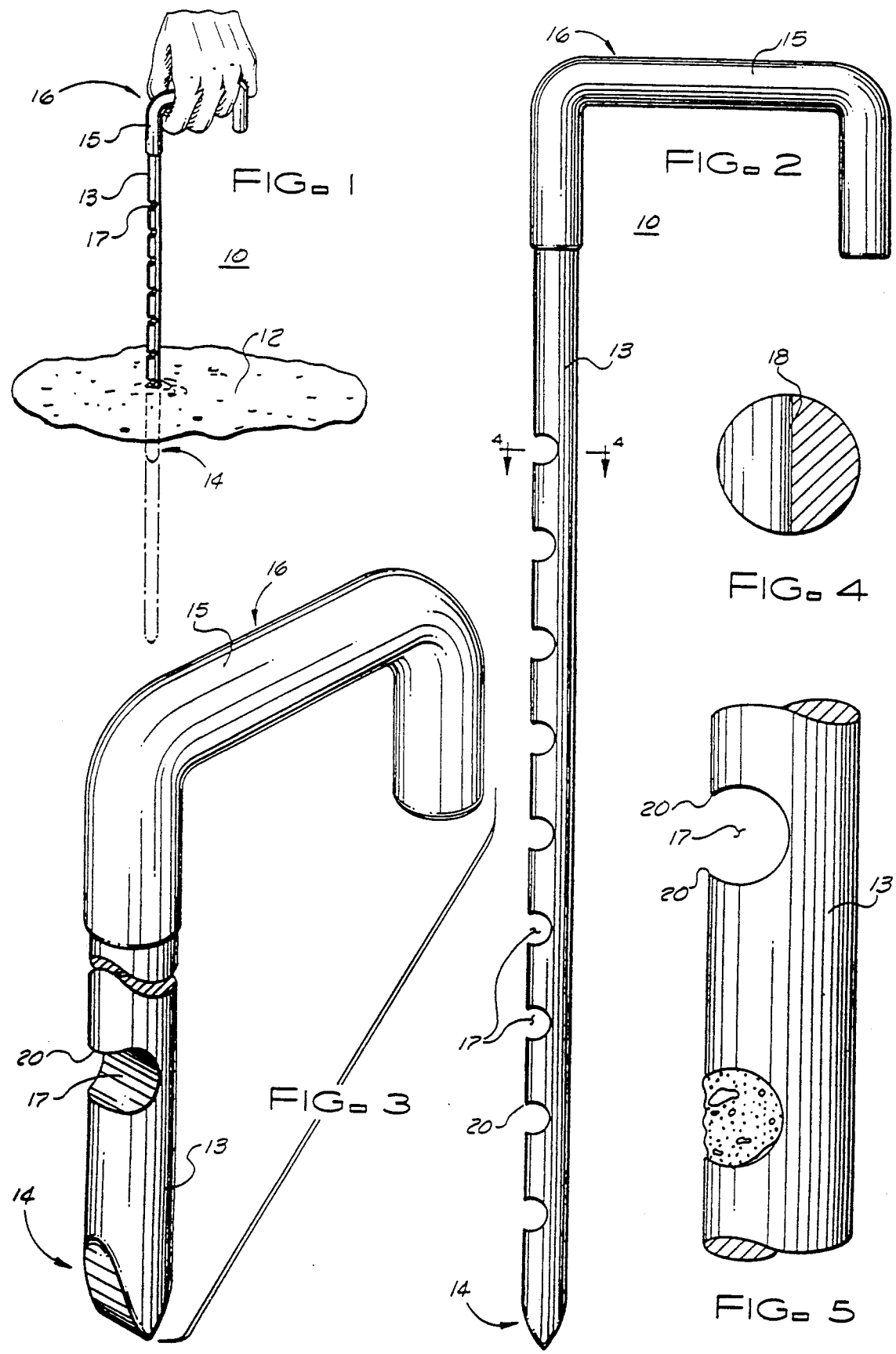

SOIL SAMPLING TOOL

BACKGROUND OF THE INVENTION

1. Field of the Invention

This invention relates to a soil sampling device.

More particularly, this invention relates to a simple, hand held tool for obtaining soil samples at moderate depths.

2. Prior Art

Soil samples are necessary for many horticultural ventures such as gardening or raising potted plants. The sample yields a variety of information including moisture content and soil structure or make-up. Tools used for obtaining soil samples are generally cumbersome, difficult to use and maintain, expensive and generally unsuitable for domestic use. Many times frequent sampling is necessary, especially when moisture content is the factor being determined. Therefore, a tool which can obtain a sample quickly and which is easily cleaned is desirable.

In garden plots or flower beds moisture in the sample may vary a great deal depending on the depth at which the sample is taken. Therefore, compartments are generally used to obtain soil samples from different depths. Typical problems with obtaining samples in these compartments are reducing contamination from soil at depths other than the sample depth, and preventing the loss of the sample from the compartment when the tool is withdrawn from the soil. Retaining sample integrity in each compartment will reduce contamination of the sample from soil at different depths.

It would be highly advantageous, therefore, to remedy the foregoing and other deficiencies inherent in the prior art.

Accordingly, it is an object of the present invention to provide an improved soil sampling tool.

Another object of the present invention is to provide a relatively inexpensive soil sampling tool.

And another object of the present invention is to provide a tool for sampling soil which can be used quickly and easily.

Still another object of the invention is to provide a soil sampling tool which can be easily cleaned after use.

Yet another object of the invention is to provide a soil sampling tool which obtains samples from varying depths.

Yet still another object of the present invention is to retain the integrity of each sample taken when the tool is withdrawn from the soil.

SUMMARY OF THE INVENTION

The invention is a tool which can be easily used by one person to obtain samples of soil from varying depths. The samples relay information on the condition of the subsurface soil, such as moisture content and soil structure. To achieve the desired objects of the present invention in accordance with a preferred embodiment thereof, provided is a cylindrical rod having an insertable end and a handle at a handle end opposite the insertable end. A plurality of collecting pockets are serially spaced along the length of and defined by the cylindrical rod. Each collecting pocket extends tangentially through the cylindrical rod and has a lip to retain sample integrity.

BRIEF DESCRIPTION OF THE DRAWINGS

The foregoing and further and more specific objects and advantages of the instant invention will become readily apparent to those skilled in the art from the following detailed description of the preferred embodiment thereof taken in conjunction with the drawings in which:

FIG. 1 is a perspective view of an embodiment of the present invention being inserted into a section of ground to obtain a soil sample;

FIG. 2 is a side view of the preferred embodiment of the present invention;

FIG. 3 is a partial perspective view of the present invention to illustrate the preferred shape of the collecting pockets;

FIG. 4 is a cross-sectional view taken on line 4—4 of FIG. 2 showing the collecting pockets; and FIG. 5 is a partial side view of a preferred embodiment of the present invention illustrating the profile shape of the collecting pockets.

DESCRIPTION OF THE PREFERRED EMBODIMENT

Turning now to the drawings in which like reference characters indicate corresponding elements throughout the several views, attention is first directed to FIG. 1 which illustrates a soil sampling tool generally designated 10 being inserted by hand into a substrate 12. Referring now to FIG. 2, sampling tool 10 has a cylindrical rod 13 with an insertably end 14 and a handle 15 extending from a handle end 16 opposite insertable end 14. A plurality of collecting pockets 17 are formed serially along the length of cylindrical rod 13. Those skilled in the art will understand that insertable end 13 may be any of a variety of shapes which facilitate entry into substrate 12, such as conical or, as in the preferred embodiment, wedge shaped. Handle 15 provides a grip through which pressure is applied by hand to cylindrical rod 13, and through which a twisting motion is imparted to cylindrical rod 13. The pressure inserts cylindrical rod 13 into the substrate to be sampled, and the twisting motion fills collecting pockets 17 with the samples. Those skilled in the art will understand that a variety of handles may be used. In the preferred embodiment a single hand grip is employed, and extends perpendicularly from handle end 16 of cylindrical rod 13. However, a two handed grip could be used, wherein a handle extends perpendicularly across handle end 16 of cylindrical rod 13. In the preferred embodiment, handle 15 is covered by a material such as plastic to provide a more secure grip.

The length of cylindrical rod 13 may vary depending on the depth of the samples required. However, the present invention is generally for obtaining samples at moderate depths. The diameter of cylindrical rod 13 must be sufficient to define collecting pockets 17 and retain structural rigidity. Tool 10 may be constructed of any material that will maintain a rigid structure when inserted and withdrawn from a substrate.

Referring to FIG. 5, it can be seen that collecting pockets 17 have a arcuate vertical profile, one side of which is open, in this embodiment. Collecting pockets 17 extend tangentially across cylindrical rod 13, and as can be seen in FIG. 4, the back of collecting pockets 17 form a tangent line 18 which cross generally near the axis of cylindrical rod 13 in the preferred embodiment. Tangent line 18 may vary, depending on the size of collecting pockets 17 and the diameter of cylindrical rod 13. If the size of collecting pockets 17 are smaller, tangent line 18 will cross cylindrical rod 17 before its axis, and if bigger, will cross past the axis. However, if collecting pockets 17 are bigger in relation to the diameter of cylindrical rod 13, then tangent line 18 must be near enough to the axis so that cylindrical rod 13 will retain its rigidity. Collecting pockets 17 have a arcuate vertical profile so that a lip 20 is formed when defined by cylindrical rod 13. This only occurs when the profile of collecting pockets 17 appear as more than 180°. This feature greatly assists in the procuring of soil on insertion of the tool 10 and maintains the integrity of the sample tool 10 is retrieved. In the preferred embodiment, the vertical profile of each collecting pocket 17 is an arc of a circle having a 9/32" diameter. While this is the preferred diameter, one skilled in the art will understand smaller or larger diameters could be used.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

I claim:

1. A soil sampling tool comprising:
   a cylindrical rod having an insertable end and a handle end opposite said insertable end;
   a handle at said handle end;
   a plurality of collecting pockets spaced serially along the length of and defined by said cylindrical rod, each of said pockets having
   an open front end; and
   a rear wall having an arcuate vertical profile; wherein
   said vertical profile being an arc of a circle tangential to a common line parallel to the longitudinal axis of said cylindrical rod, and having a diameter parallel to the longitudinal axis of said rod, said arc measuring greater than 180°;
   wherein said rod is inserted into a substrate and twisted to drive soil into said collecting pockets, and subsequently withdrawn from said substrate to provide a soil sample.

2. A device as claimed in claim 1, wherein portions of said rear wall extend forwardly of said diameter, said portions projecting vertically to form lips framing said open side for retaining soil in said pocket.

* * * * *